United States Patent [19]

Hogan et al.

[11] 4,126,632

[45] Nov. 21, 1978

[54] DIMERIZATION PROCESS

[75] Inventors: Philip J. Hogan; James R. Jennings, both of Runcorn, England

[73] Assignee: Imperial Chemical Industries Limited, London, England

[21] Appl. No.: 736,498

[22] Filed: Oct. 28, 1976

[30] Foreign Application Priority Data

Oct. 31, 1975 [GB] United Kingdom ............... 45324/75
Dec. 24, 1975 [GB] United Kingdom ............... 52888/75

[51] Int. Cl.² .................. C07C 120/00; C07C 121/20
[52] U.S. Cl. ............................................ 260/465.8 D
[58] Field of Search ................................. 260/465.8 D

[56] References Cited

U.S. PATENT DOCUMENTS 3,538,141  11/1970  Kollar ............................... 260/465.8
3,574,702  4/1971  Feldman et al. .................. 260/465.8

FOREIGN PATENT DOCUMENTS 644,774  3/1964  Belgium.
1,519,376  2/1968  France.
1,597,593  6/1970  France.
1,385,883  12/1974  France ............................... 260/465.8 D
1,003,656  9/1965  United Kingdom.
1,051,821  12/1966  United Kingdom.
1,128,320  9/1968  United Kingdom.
1,154,275  6/1969  United Kingdom.
1,351,694  5/1974  United Kingdom.

*Primary Examiner*—Joseph Paul Brust
*Attorney, Agent, or Firm*—Cushman, Darby & Cushman

[57] ABSTRACT

Process for the dimerization of acrylonitrile to predominantly straight-chain 1,4-dicyanobutenes (DCB). The ACN is contacted with an organic phosphinite or phosphonite in the presence of an inert proton-donating solvent and, optionally, an inert non-hydroxylic co-solvent preferably a hydrocarbon, the ACN and solvent(s) being substantially dry. Selectivities of 95% are obtained with respect to 1,4 - DCB.

9 Claims, No Drawings

DIMERIZATION PROCESS

This invention relates to a dimerisation process and, especially, to a process for the dimerisation of acrylonitrile to linear $C_6$ dinitriles.

It is known to dimerise acrylonitrile in the presence of hydroxylic compounds, such as alcohols, phenols or water, using tervalent organo-phosphorus compounds, such as, tertiary phosphines $PR_3$ or phosphites $P(OR)_3$, as catalyst. However, the principal product of such reactions is commonly internally substituted 2,4-dicyanobutene-1 (2-methylene glutaronitrile).

It has already been proposed, for example in British Pat. specification No. 1,018,220, to dimerise acrylonitrile in the presence of an organic tertiary phosphine catalyst to give as the principal product 1,3-dicyanobutene-3, otherwise known as 2,4-dicyanobutene-1 or 2-methyleneglutaronitrile. There is a commercial demand, however, for 1,4-dicyanobutenes since these are directly convertible by successive hydrogenation into adiponitrile and hexamethylene diamine, but these 1,4-isomers are not reported as being obtained in major amount under normal conditions with the usual phosphine catalysts. British Pat. specification No. 1,051,821 has proposed to dimerise acrylonitrile using equally either organic phosphine or organic phosphite catalysts to give products said to be mixtures containing mainly 2-methylene glutaronitrile with some 1,4-dicyanobutenes.

We have now found that the straight chain 1,4-dicyanobutenes, may be produced with high selectivity using specified organic phosphorus (III) compounds in the substantial absence of water but in the presence of suitable solvents.

According to the present invention, a process for the dimerisation of acrylonitrile to predominantly straight chain $C_6$ dimers comprises contacting the acrylonitrile with an organic phosphorus (III) compound which has at least one hydrocarbyl and at least one alkoxy or cycloalkoxy group attached to the phosphorus atom or atoms, the acrylonitrile being dissolved in an organic solvent capable of donating protons and the acrylonitrile and solvent being substantially dry.

Suitable organic phosphorus (III) compounds include those of general formulae:-

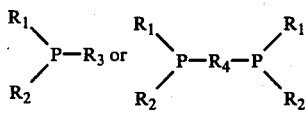

where $R_1$ is a hydrocarbyl group, $R_2$ is an alkoxy or cycloalkoxy group, $R_3$ is hydrocarbyl, alkoxy or cycloalkoxy group or other monovalent radical, and $R_4$ is a divalent hydrocarbyl, hydrocarbyloxy or other difunctional group. It is also possible that one or more groups $R_1$ to $R_3$ may form part of one or more ring systems..

The hydrocarbyl groups may be aryl, alkyl, alkaryl, aralkyl or cycloalkyl.

High proportions of straight-chain dimers are obtained where each hydrocarbyl group is aryl, in the case where either 1 or 2 hydrocarbyl groups are present in the phosphorus (III) compound. High reaction rates are obtained where one or both of the hydrocarbyl groups is alkyl in cases where two hydrocarbyl groups are present; but these high reaction rates may be accompanied by somewhat lower proportions of straight-chain dimers than where both hydrocarbyl groups are simple aryl. The hydrocarbyl groups may contain substituents, suitable substituent groups being halogen, cyanide, alkyl and alkoxy. High rates may also be achieved by the use of substituted aryl groups, for example, p-methoxyphenyl. The alkoxy or cycloalkoxy group or groups may contain similar substituents and may also contain aryl substituents. Examples of suitable alkoxy groups include methoxy, ethoxy, benzyloxy and isopropoxy.

Suitable examples of divalent groups $R_4$ include alkylene, polyalkylene and phenylene and poly phenylene groups, alkylene dioxy and polyalkylene dioxy groups.

Groups $R_1$ to $R_4$ may also be part of a polymeric backbone, for example polystyrene or polyvinyl alcohol, or be linked to an inorganic support, for example silica or alumina.

Provided that the groups $R_1$ to $R_4$ do not give rise to undesirable steric effects there is no finite limit on the number of carbon atoms they may contain. However, they will commonly contain from 1 to 10 carbon atoms.

It will be appreciated from the above that in the phosphorus (III) compounds which are useful in our invention each phosphorus atom must have at least one hydrocarbyl and one alkoxy group attached to it, but must not bear either only hydrocarbyl or only alkoxy groups. Preferred examples of phosphorus (III) compounds are phosphinites and phosphonites.

Examples of suitable phosphorus (III) compounds include diethyl phenylphosphonite, dimethyl phenylphosphonite; dimethyl p-methylphenylphosphonite, diethyl p-methylphenylphosphonite, methyl diphenylphosphinite, isopropyl diphenylphosphinite, ethyl phenylethylphosphinite, ethyl diphenylphosphinite, cyclohexyl diphenylphosphinite, diethyl p-tolylphosphinite, 2-ethylhexyl diphenylphosphinite, bis(2-ethylhexyl) phenylphosphonite, di(isopropyl) phenylphosphonite, di(neopentyl) phenylphosphonite, 2-octyl diphenylphosphinite, bis(3,5,5-trimethylhexyl) phenylphosphonite, 2-methylcyclohexyl diphenylphosphinite, 3,5,5-trimethylhexyl diphenylphosphinite, sec.butyl diphenylphosphinite, cyclohexyl diphenylphosphinite, benzyl diphenylphosphinite, $Ph_2PO(CH_2)_4OPPh_2$,

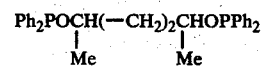

and

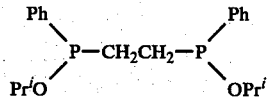

The presence of an organic solvent is essential to our process, since in the absence of solvent rapid polymerisation of the acrylonitrile occurs. Suitable solvents are protondonating solvents which are substantially unreactive in respect of addition to, or reaction with, the unsaturated linkage of the acrylonitrile or the products of acrylonitrile dimerisation. Furthermore, the solvent must not react with the phosphorus compounds or catalytic intermediates to form inactive phosphorus species at such a rate as to seriously impair the dimerisation reaction. For example, phenols have been found to be unsuitable in this respect.

Preferably hydroxylic solvents, such as alcohols, are used, provided always that they do not react adversely with the phosphorus compound or any intermediates it may form with acrylonitrile. This may be readily established by experiment. Tertiary and secondary alcohols are preferred, for example, t-butylalcohol, 2-butanol and isopropanol.

The concentration of proton-donating solvent is generally in the range 5 to 50% by volume, calculated on the total volume of the reactants, but the optimum concentration will vary with the precise nature of the solvent and the catalyst compound. The molar concentration of proton-donating solvent will generally be greater than the molar concentration of the phosphorus (III) compound.

In order to reduce the amount of hexamer and/or other oligomers or polymers (hereafter referred collectively as polymeric by-products or merely polymers) which may be co-produced with the desirred dimeric products, it is often desirable to add an inert, non-hydroxylic co-solvent to the reaction mixture used in our process. It will be apparent that the co-solvent must be dried to a level which maintains the overall anhydrous state of the system.

Suitable non-hydroxylic organic solvents include hydrocarbons, for example, hexane, cyclohexane, toluene, and petroleum ethers; ethers, for example, tetrahydrofuran, diethyl ether and diisopropyl ether; and nitriles, for example, acetonitrile, propionitrile; and fluorobenzenes. The hydrocarbon co-solvents are generally preferred.

An essential feature of the present invention is that the reaction must be conducted in the substantial absence of water. Without prejudice to our invention, we believe that the water reacts with the catalyst in the presence of acrylonitrile to give non-catalytic addition compounds. Thus, the acrylonitrile, proton-donating solvent and co-solvent must be dried before use, otherwise the reaction may be completely inhibited. In particular acrylonitrile, which commonly contains as much as 4000 ppm of water, even after distillation, must be rigorously dried. It is also noted that hydroquinone stabilisers, which are present in acrylonitrile as supplied, should be removed. For example, if the reactants contain 300 ppm of water, reaction is seriously inhibited at a concentration of the phosphorus compound of 0.5% by volume; but at water concentrations of 50 ppm or lower reaction takes place readily. Any suitable drying technique may be used, provided that the final water level is sufficiently low. For example, acrylonitrile and hydroxylic solvents may be dried by being contacted with calcium hydride or a 3A or 4A molecular sieve. The above findings contrast strongly with the teaching of the prior art which makes no mention of removal of water and/or hydroquinone stabilisers, and in many instances advocates the addition of water and stabilisers, such as hydroquinone, to the reaction mixture. It will be appreciated that at higher concentration of water, e.g. 300 ppm, it may be possible to cause the reaction to proceed by adding much larger amounts of catalyst. If this is done, selectivity is generally unaffected; but the process would become commercially unattractive because of high catalyst usage.

The concentration of acrylonitrile in the solvent or solvent mixture generally should range from 5 to 75% by volume. The concentration of acrylonitrile is kept as high as possible in order to optimise throughput and thus concentrations in the range 10 to 50% by volume are generally preferred.

The concentration of the phosphorus compound in the reactant mixture may be varied over a wide range, for example, from 0.01, commonly 0.1, to 5% by volume, calculated on the volume of liquid reactants; but preferably the concentration is in the range 0.1 to 3% by volume. When present, the proportion of co-solvent in the reaction mixture may be varied over wide limits. In general the ratio of proton-donating solvent to co-solvent is in the range 1:20 to 20:1, commonly in the range 1:9 to 9:1, but the ratios outside these limits may be used. Conveniently the said ratio is in the range 1:2 to 2:1, for example about 1:1. However, the final choice of ratio will depend on how it is desired to run the process and the choice of catalyst compound. For example, when t-butanol is used with isopropyl diphenyl phosphinite, solvent/co-solvent ratios in the range 1/1 to 1/5 are preferred. However, when isopropanol is used with isopropyl ethyl phenyl phosphinite, ratios in the range 1/3 to 1/7 are preferred; and when isopropyl diethylphosphinite is used preferred ratios are in the range 1/5 to 1/20. The above ratios are by volume.

Changes in the ratio of proton-donating solvent/co-solvent are generally reflected by changes in the amount of polymers formed and changes in the reaction rate. These changes in reaction parameters are often dependant upon the actual catalyst and solvent system chosen. For example, addition of toluene to a dimerisation system comprising acrylonitrile, tertiary butanol and isopropyldiphenylphosphinite results in a reduction in the production of polymers, but also in a reduction in the rate of reaction. The presence of a co-solvent also allows higher reaction temperatures to be used and, in some cases, has a stabilising effect on the phosphorus (III) compounds used as catalysts.

The ratio of linear to branched dimers is dependent on the solvent/co-solvent ratio in some instances. It is sometimes found that, as the proportion of proton-donating solvent decreases, the proportion of linear dimer increases and vice-versa.

The reaction temperature is commonly in the range 0° to 120° C.; but it is generally preferred to keep the range temperature below 75° C. to minimise polymerisation of the acrylonitrile and dimeric products. Preferably, the reaction temperature is in the range 20° to 70° C. It is noted that the reaction will proceed below 0° C., maintaining selectivity, but at a reduced rate.

Unlike other acrylonitrile dimerisation processes, the presence of compounds such as hydroquinone and its monomethyl ether, p-methoxyphenol, which are commonly used at present as acrylonitrile stabilisers, should be avoided.

The reaction may be carried out batchwise or continuously. In the latter case it may be convenient to support the catalyst compound or to use a polymeric tervalent phosphorus compound to enable the reaction to be carried out in the liquid phase using a heterogeneous catalyst.

The dimeric products of our invention are predominantly linear $C_6$ dinitriles, especially the 1,4-dicyanobutenes. Selectivities > 90 wt % (calculated on total dimeric product) may be readily obtained and selectivities as high as 98% have been obtained using our most advantageous catalysts.

The desired products may be readily separated from the reaction mixture for example by fractional distillation or solvent extraction.

The invention will be illustrated by the following Examples, in which all parts are by weight.

In all the Examples, except where otherwise stated, the acrylonitrile was dried before use by means of calcium hydride. This was accomplished by adding powdered calcium hydride to the acrylonitrile overnight, then decanting the acrylonitrile on to fresh calcium hydride powder and refluxing for 30 minutes. The acrylonitrile was then distilled from the calcium hydride. Water levels were found to be in the range 30–80 ppm after this procedure. The acrylonitrile was dried finally by storing over freshly activated 3A molecular sieve to give levels below 15 ppm.

The phosphorus (III) compounds used in the Examples are either commercially available or were prepared using methods given in "Organo-Phosphorus Compounds", Kosolapoff and Maier published by Wiley 1972, Vol 4, Chapters 10 and 11.

All analyses of dimeric products were made by gas chromatography.

In all the Examples, "% conversion" indicates the % by weight of acrylonitrile (ACN) converted to total dimeric, oligomeric and polymeric products; the "% yield" of a product is the weight of that product calculated as a % of the weight of ACN converted; and the "Selectivity" or "% linear" is the proportion of straight-chain or linear dimers, calculated on the total dimeric product.

EXAMPLE 1

Acrylonitrile (40 parts), t-butanol (40 parts) and diethyl phenylphosphonite, PhP(OEt)$_2$ (0.9 part) were mixed at room temperature and heated, with stirring, up to 60° C. over a period of half an hour. The mixture was kept at this temperature for a further hour and was then filtered to remove 1 part of a white crystalline solid (probably hexamer). The filtrate was then vacuum distilled to remove solvent and unreacted acrylonitrile, leaving a less volatile liquid fraction (15 parts). Analysis showed the liquid to contain acrylonitrile dimers in the proportion 96% cis and trans 1,4-dicyanobutene-1 (1,4 DCB-1) and 4% methylene glutaronitrile (MGN).

When the procedure was repeated with triphenyl phosphine as catalyst, very low conversions were obtained and the DCB:MGN ratio was 4:1.

The general procedure of Example 1 was repeated using diethyl ether in place of t-butanol. A large amount of a white precipitate formed; and very small quantities of dimers were detected. When the procedure was repeated in the absence of solvent, there was an induction period of a few seconds followed by violent polymerisation of the acrylonitrile, leaving no liquid product in the reactor.

EXAMPLE 2

Acrylonitrile (40 parts), t-butanol (40 parts) and dimethyl phenylphosphonite, PhP(OMe)$_2$ (0.9 part) were mixed at room temperature with stirring. Over a 30 minute period the temperature of the mixture rose spontaneously from 22° C. to 32° C., its colour becoming yellow with formation of a fine precipitate. The mixture was left for 6 days, after which the solid (4.25 parts) was removed by filtration. Unreacted acrylonitrile and t-butanol were removed by distillation leaving 10.3 parts of residue. Analysis showed the mixture to contain 38.8% cis 1,4 DCB-1, 53.5% trans 1,4 DCB-1 and 7.8% MGN.

The procedure of Example 2 was repeated with the addition of 0.5 parts of (a) p-methoxy phenol and (b) hydroquinone, both commonly-used acrylonitrile stabilisers. In each case traces of hexamer were produced, but no dimers.

When the procedure of Example 2 was repeated using phenyl diphenyl phosphinite, Ph$_2$POPh, as catalyst, there was no colour change and only trace amounts of dimers were detected, although the linear/branched ratio was similar.

Furthermore, when tribenzyl phosphine was used as catalyst, analysis of the products indicated that dimerisation had proceded very slowly, and branched dimer predominated.

EXAMPLE 3

The procedure used in Example 2 was followed except that the catalyst used was dimethyl p-methylphenylphosphonite, p-Me C$_6$H$_4$ P(OMe)$_2$. 1.25 parts of hexamer and 8.75 parts of product containing dimers were obtained. Analysis showed the dimers to be present in the ratio cis 1,4 DCB-1 trans 1,4 DCB-1:MGN = 37.85:60.0:2.15.

When the procedure was repeated with the addition of 0.05 parts of water, dimer formation was inhibited; also no propionitrile was formed.

EXAMPLE 4

Acrylonitrile (16 parts), t-butanol (16 parts), toluene (16 parts) and dimethyl p-methylphenylphosphonite, CH$_3$C$_6$H$_4$P(OMe)$_2$ (0.36 parts) were mixed at room temperature and heated over a period of 1 hour to 70° C. Analysis showed that dimers had been formed, and that the DCB-1:MGN ratio was 93:7.

EXAMPLE 5

The procedure used in Example 2 was followed except that the catalyst used was diethyl p-methylphenylphosphonite CH$_3$C$_6$H$_4$P(OEt)$_2$ and that the t-butanol had been distilled from calcium hydride. 0.75 parts of hexamer and 14.8 parts of a non-volatile liquid were obtained. Analysis showed dimers to be present and the DCB-1:MGN ratio to be 95:5.

EXAMPLE 6

Acrylonitrile (40 parts), n-butanol (40 parts) and methyl diphenylphosphinite Ph$_2$POMe (1.3 parts) were mixed together at room temperature and heated to 120° C. over a period of 1.5 hours. The ratio of linear to branched dimers was 16:1, and a minor proportion of hexamer was obtained.

EXAMPLE 7

The procedure used in Example 6 was followed except that t-butanol was used as solvent and that the maximum temperature was limited to 75° C. The ratio of linear to branched dimers was 24:1, and a minor proportion of hexamer was obtained.

When the procedure of Example 7 was repeated using, in place of t-butanol, analytical grade methanol which had been dried over magnesium turnings by standard procedures, only trace amounts of dimers were detected in the products.

EXAMPLE 8

The procedure used in Example 6 was followed with isopropyl diphenylphosphinite $Ph_2POPr^{iso}$ catalyst and t-butanol solvent. The temperature was limited to 80° C. The ratio of linear to branched dimers was 16:1, and a minor proportion of hexamer was obtained.

EXAMPLE 9

Acrylonitrile (16 parts), t-butanol (48 parts) and isopropyl diphenylphosphinite, $Ph_2POPr^{iso}$ (0.35 parts) were stirred together at room temperature. After work up, 1.9 parts of hexamer and 8.1 parts of a dimer-containing non-volatile liquid were obtained. The ratio of linear to branched dimers was 92.5:7.5.

EXAMPLE 10

Acrylonitrile (16 parts, dried by a 3A Molecular Sieve), t-butanol (16 parts, dried by a 3A Molecular Sieve) and ethyl (phenyl) ethylphosphinite Ph(Et)POEt (0.4 parts) were mixed at room temperature and stirred for 4 hours. A dimer-containing liquor (5 parts) was obtained. The ratio of linear to branched dimers being 58:42. Some hexamer (1.5 parts) was also obtained.

EXAMPLES 11-15

A stock solution was prepared by mixing equal volumes of acrylonitrile, tertiary butanol (decanted from a molecular sieve) and toluene (distilled from triethyl aluminium) and the solution was then stored over a 3A molecular sieve.

Portions of this solution (150 ml) were then heated to reflux the temperature on a water bath and the appropriate phosphorus (III) compound catalyst added by syringe under an atmosphere of notrogen. The reflux temperature was maintained for 5 hours, after which time any precipitated solid polymer was removed by filtration and the mixed solvent and unreacted monomer removed by evaporation.

A second stock solution was prepared by mixing equal volumes of acrylonitrile and tertiary butanol, dried and stored as previously described. A series of comparative experiments was carried out using portions of this second stock solution and appropriate phosphorus III compound catalysts and subjecting them to the same general procedure.

Results are set out in Table I, from which it will be seen that the presence of the co-solvent reduced the proportion of solid polymer and increased the proportion of dimers in the product.

EXAMPLES 16 and 17

The procedure of Examples 11-15 was followed except that toluene was replaced by hexane in the stock solution. The results are shown in Table 2.

The catalysts used in the Examples are identified by the letters A-D, as follows:

A — Isopropyl diphenyl phosphinite
B — Ethyl diphenyl phosphinite
C — Cyclohexyl diphenyl phosphinite
D — Diethyl p-tolyl phosphonite The "m moles of catalyst" in the Tables signifies millimoles of catalyst per 150 ml of reaction mixture.

EXAMPLE 18

The general procedure of Examples 1 to 5 was carried out; but tetrahydrofuran was used in the place of toluene in the stock solution. The catalyst used was 4.1 m moles of catalyst A. The yield of dimers was 75%, solid polymer 8.7% and conversion 19%. This should be compared with comparative example C1.

Table 1

| Ex. No. | Catalyst | m moles catalyst | % conversion | Yield of Dimers | % solid polymer |
|---|---|---|---|---|---|
| 11 | A | 4.23 | 53 | 85 | 5.5 |
| *C11 | A | 4.06 | 59 | 63 | 15.4 |
| 12 | B | 4.15 | 63 | 89 | 4.1 |
| C12 | B | 4.14 | 65 | 51 | 20.8 |
| 13 | C | 3.52 | 52 | 92 | 3.2 |
| C13 | C | 3.52 | 57 | 65 | 14.5 |
| 14 | D | 3.61 | 50 | 92 | 3.2 |
| C14 | D | 3.95 | 48 | 73 | 10.8 |
| 15 | B | 2.34 | 46 | 90 | 3.7 |

*C1-4 are comparative Examples

Table 2

| Ex. No. | Catalyst | m moles catalyst | % conversion | % Yield of Dimers | % solid polymer |
|---|---|---|---|---|---|
| 16 | B | 3.78 | 29 | 91 | 3.5 |
| 17 | A | 4.40 | 39 | 93 | 2.6 |

EXAMPLES 19-33

Equal volumes of acrylonitrile, toluene and t-butanol were mixed and heated to reaction temperature in a closed vessel. The appropriate catalyst was then injected and the reaction mixture maintained at reaction temperature for the time stated. At the end of this time, the reaction was terminated by the addition of a small quantity of water and any hexamer and/or solid polymer filtered off. Both solvents and unreacted acrylonitrile were removed by vacuum distillation at ambient temperature. The residue, which comprised dimers, oily oligomers and catalyst residues, was analysed by g.l.c. against an external standard. Results are shown in Table 3.

Table 3

| Ex No | Catalyst | Wt (m.mole) | ACN (g) | Temp (° C) | Time (hrs) | % Conv. | % Linear | % Yield 1,4-DCB | Hexamer | MGN |
|---|---|---|---|---|---|---|---|---|---|---|
| 19 | $Ph_2PO(Ethexyl)$ | 3.25 | 38 | 62 | 22 | 34 | 95.8 | 78 | 4 | 3.3 |
| 20 | " | 2.08 | 31 | 62 | 22 | 24 | 95.5 | 76 | 3 | 3.4 |
| 21 | $PhP(O-Ethexyl)_2$ | 2.56 | 36 | 62 | 22 | 42 | 97.5 | 56 | 5 | 1.4 |
| 22 | " | 1.36 | 37 | 62 | 22 | 21 | 96.4 | 53 | 3 | 1.9 |
| 23 | $Ph_2PO(isoPr)$ | 2.45 | 37 | 62 | 22 | 32 | 92.7 | 62 | 9 | 4.5 |
| 24 | " | 4.63 | 40 | 62 | 22 | 63 | 92.7 | 53 | 16 | 3.9 |
| 25 | $PhP(O-isoPr)_2$ | 2.44 | 19 | 60 | 4 | 45 | 92.0 | 52 | 8 | 4.2 |
| 26 | $Ph_2PO(CHCMe_3)$ | 1.98 | 19 | Reflux | 3.5 | 21 | 94.7 | 77 | 1 | 4.1 |
| 27 | $Ph_2PO(OCH_2CMe_3)_2$ | 3.35 | 38 | 64 | 4 | 22 | 97.0 | 66 | 2 | 2.0 |
| 28 | " | 1.95 | 20 | 64 | 4 | 28 | 97.2 | 68 | 2 | 1.9 |
| 29 | $Ph_2PO(2-Octyl)$ | 2.94 | 41 | Reflux | 3.5 | 12 | 90.9 | 64 | 7 | 6.3 |
| 30 | " | 1.35 | 20 | Reflux | 3.5 | 12 | 91.4 | 58 | 4 | 5.0 |
| 31 | $PhP(O-Nonyl)$ | 2.29 | 38 | 64 | 4 | 9 | 93.4 | 70 | 5 | 4.6 |
| 32 | $Ph_2PO$ | 1.99 | 19 | 60 | 4 | 16 | 90.4 | 60 | 4 | 5.8 |

Table 3-continued

| Ex No | Catalyst | Wt (m.mole) | ACN (g) | Temp (° C) | Time (hrs) | % Conv. | % Linear | % Yield 1,4-DCB | Hexamer | MGN |
|---|---|---|---|---|---|---|---|---|---|---|
| 33 | 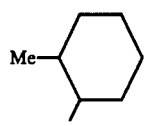Ph(Et)POEt | 3.12 | 20 | 60 | 4 | 16 | 78.0 | 43 | 7 | 13 |

Notes on Table 3
Me = methyl: Et = ethyl: Pr = propyl: Ph = phenyl Nonyl = 3,5,5 trimethylhexyl.

EXAMPLES 34–43

The general procedure of Examples 19–33 was used with 1g of catalyst and 50 ml each of acrylonitrile and t-butylalcohol. 50 ml of toluene was added in Examples 41–43. In the work-up of the product, volatiles were removed on a rotavapour and the residue analysed by g.l.c. Results are shown in Table 4.

Table 4

| Ex No | Catalyst | Temp. | Time (hrs) | % Selectivity |
|---|---|---|---|---|
| 34 | Ph$_2$PO(sec Bu) | A | 24 | 90.7 |
| 35 | Ph$_2$PO(c Hex) | A | 24 | 93.6 |
| 36 | Ph$_2$PO(iso Pr) | A | 24 | 93.3 |
| 37 | Ph$_2$PO(sec Bu) | A | 8½ | 93.0 |
| 38 | " | R | 3 | 87.3 |
| 39 | Ph$_2$PO(c Hex) | R | 3 | 87.2 |
| 40 | Ph$_2$PO(Bz) | R | 3 | 91.5 |
| 41 | Ph$_2$PO(sec Bu) | R | 5 | 90.8 |
| 42 | Ph$_2$PO(c Hex) | R | 5 | 91.8 |
| 43 | Ph$_2$PO(sec Bu) | A | 96 | 95.8 | sec Bu = Sec. butyl : c Hex = cyclohexyl : Bz = benzyl
A = ambient temp. : R = reflux temp.

EXAMPLES 44–55

These Examples show the effect of varying the ACN/proton-donating solvent/co-solvent ratio.

The volumes of ACN, isopropyl alcohol (IPA) and toluene shown in Table 5 were mixed at ambient temperature. The appropriate catalyst (Ph(Et)PO(isoPr) for Examples 44–49 and Ph(Et)PO(Et) for Examples 50–55) was added in the amount stated and reaction allowed to proceed at ambient temperature for 1 hour. Reaction was terminated by addition of water, volatiles evaporated under vacuum and product analysed by g.l.c.

Results are shown in Table 5.

Table 5

| Ex No | Wt. of Catalyst (g) | Volume (me) ACN | Toluene | IPA | % Conversion | % Linear | Yield 1,4 DCB | MGN | Hexamer |
|---|---|---|---|---|---|---|---|---|---|
| 44 | 0.16 | 10.1 | 9.9 | 9.3 | 70 | 72 | 24 | 9 | 32 |
| 45 | 0.15 | 9.8 | 9.3 | 5.1 | 24 | 83 | 50 | 11 | 18 |
| 46 | 0.38 | 9.7 | 9.9 | 2.3 | 90 | 84 | 37 | 7 | 16 |
| 47 | 0.19 | 9.9 | 9.8 | 1.2 | 26 | 86 | 63 | 10 | 2 |
| 48 | 0.25 | 4.2 | 9.8 | 1.2 | 56 | 86 | 64 | 10 | 8 |
| 49 | 0.36 | 5.4 | 9.7 | 1.4 | 37 | 87 | 64 | 9 | 2 |
| 50 | 0.18 | 9.7 | 10.0 | 10.0 | 62 | 74 | 28 | 10 | 31 |
| 51 | 0.23 | 9.7 | 10.0 | 5.0 | 71 | 78 | 37 | 10 | 26 |
| 52 | 0.26 | 9.3 | 10.0 | 2.0 | 70 | 87 | 49 | 7 | 13 |
| 53 | 0.22 | 9.7 | 10.0 | 1.0 | 51 | 87 | 57 | 9 | 7 |
| 54 | 0.28 | 4.0 | 10.0 | 2.0 | 71 | 87 | 62 | 10 | 8 |
| 55 | 0.15 | 4.6 | 10.0 | 1.0 | 38 | 89 | 65 | 8 | 4 |

EXAMPLES 56–62

Mixtures of acrylonitrile, toluene and an alcohol were made up in the proportions shown in Table 6. A catalytic quantity of isopropyl diethyl phosphinite was added to each mixture and its temperature maintained at 23° C. for the time indicated to allow reaction to take place. The dimeric products were analysed by quantitative g.l.c., the results being shown in Table 6. Isopropanol was used in all except Example 57, in which methanol was used; 0.1g of catalyst was used in all except Examples 60 and 61, in which 0.025g was used.

Table 6

| Ex No. | ACN (ml) | Toluene (ml) | Alcohol (ml) | Time (min) | Wt. of Dimeric Products(g) 1,4DCB | MGN | % Linear |
|---|---|---|---|---|---|---|---|
| 56 | 10 | 16 | 0.3 | 60 | 0.86 | 0.28 | 75 |
| 57 | 10 | 16 | 0.7 | 120 | 0.69 | 0.05 | 94 |
| 58 | 2.5 | 16 | 1.3 | 30 | 0.99 | 0.15 | 87 |
| 59 | 2.5 | 16 | 1.3 | 120 | 1.29 | 0.19 | 87 |
| 60 | 2.5 | 23 | 1.3 | 30 | 0.27 | 0.04 | 87 |
| 61 | 2.5 | 23 | 1.3 | 120 | 0.33 | 0.05 | 87 |
| 62 | 10 | 16 | 1.3 | 15 | 1.12 | 0.27 | 81 |

EXAMPLES 63–70

ACN, isopropanol (except Examples 69 and 70 in which butanol was used) and toluenes were mixed in the volumes stated and heated to reaction temperature. Isopropyl bis p-methoxyphenyl phosphinite was added in the amount stated and the temperature maintained for the stated time. The reaction was then killed by the addition of water, volatiles removed at room temperature under vacuum and the dimeric product analysed by g.l.c. Results are given in Table 7.

Table 7

| Ex. No. | Cat. (g) | ACN (ml) | Alc. (ml) | Tol. (ml) | Time (min) | Temp (° C) | % Convn | % Linear | % Yield 1,4 DCB | MGN | Hexamer |
|---|---|---|---|---|---|---|---|---|---|---|---|
| 63 | 0.10 | 5 | 2.0 | 10 | 90 | 20 | 19 | 91 | 66 | 7 | 7 |
| 64 | 0.33 | 5 | 1.0 | 10 | 90 | 20 | 46 | 92 | 71 | 6 | 5 |
| 65 | 0.35 | 5 | 0.5 | 10 | 90 | 20 | 34 | 92 | 70 | 6 | 2 |

Table 7-continued

| Ex. No. | Cat. (g) | ACN (ml) | Alc. (ml) | Tol. (ml) | Time (min) | Temp (°C) | % Convn | % Linear | % Yield 1,4 DCB | MGN | Hexamer |
|---|---|---|---|---|---|---|---|---|---|---|---|
| 66 | 0.36 | 5 | 0.5 | 10 | 30 | 60 | 56 | 88 | 51 | 7 | 3 |
| 67 | 0.33 | 5 | 1.5 | 10 | 30 | 60 | 74 | 89 | 77 | 9 | 4 |
| 68 | 0.35 | 5 | 2.0 | 10 | 120 | 0 | 25 | 92 | 82 | 7 | 8 |
| 69 | 0.34 | 10 | 10 | 10 | 90 | 20 | 63 | 88 | 62 | 8 | 6 |
| 70 | 0.37 | 5 | 2.0 | 10 | 90 | 60 | 40 | 91 | 63 | 6 | 1 |

EXAMPLES 71–72

The general procedure of Examples 19–33 was followed, using as catalyst 1g of tetramethylene bis diphenyl phosphinite (Ex.71) or diethyl-p-chlorophenyl phosphonite (EX.72). Reaction was maintained at reflux temperature for 5 hours and analysis of the dimeric products by g.l.c. showed that conversions were approximately 18% and 25% while selectivities to linear products were 94.8 and 96.4 respectively.

We claim:

1. A process for the dimerisation of acrylonitrile to obtain a product which is predominantly 1,4-dicyanobutenes, comprising:

dissolving acrylonitrile in an organic solvent capable of donating protons but substantially unreactive with respect to acrylonitrile and organic phosphorus (III) compounds, and contacting acrylonitrile with an organic phosphorus (III) compound having the formula:

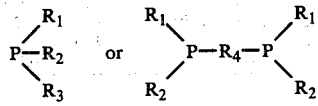

where $R_1$ is hydrocarbyl as such or substituted with halogen, cyanide or alkoxy, $R_2$ is alkoxy or cycloalkoxy, $R_3$ is hydrocarbyl as such or substituted with halogen, cyanide or alkoxy, alkoxy or cycloalkoxy, and $R_4$ is divalent hydrocarbyl as such or substituted with halogen, cyanide or alkoxy, or hydrocarbyloxy, the carbon content of each of the groups $R_1$ to $R_4$ being from 1 to 10, at a temperature from 0° to 120° C., the concentrations of acrylonitrile and said organic phosphorus (III) compound being in the ranges 5 to 75% and 0.01% to 5% by volume, respectively, and the acrylonitrile and solvent being essentially dry and free of phenolic acrylonitrile stabilisers, the product thus obtained containing at least 58% 1,4-dicyanobutenes.

2. A process as claimed in claim 1 in which the water level of the reaction mixture is < 50 ppm.

3. A process as claimed in claim 1 in which at least one of $R_1$ and $R_3$ is an aryl group.

4. A process as claimed in claim 1 in in which the phosphorus (III) compound is selected from diethyl phenylphosphonite, dimethyl phenyl phosphonite, dimethyl p-methyl phenyl phosphonite, diethyl p-methylphenyl phosphonite, methyl diphenyl phosphinite, isopropyl diphenyl phosphinite, ethyl (phenyl) ethyl phosphinite, ethyl diphenyl phosphinite, cyclohexyl diphenyl phosphinite, diethyl p-tolyl phosphonite, ethyl hexyl diphenyl phosphinite, di(ethyl hexyl) phenyl phosphonite, di(isopropyl) phenyl phosphonite, di(neopentyl) phenyl phosphonite, 2-octyl diphenyl phosphinite, di(3,5,5 trimethyl hexyl) phenyl phosphonite, O-methyl phenyldiphenyl phosphinite, 3,5,5 trimethyl hexyl diphenyl phosphinite, sec.butyl diphenyl phosphinite, cyclohexyl diphenyl phosphinite, benzyl diphenyl phosphinite.

5. A process as claimed in claim 1 in which an inert, non-hydroxylic co-solvent is added to the reaction mixture.

6. A process as claimed in claim 5, in which the co-solvent is a hydrocarbon.

7. A process as claimed in claim 1 in which the concentration of the phosphorus III compound in the reaction mixture is from 0.1 to 3% by volume.

8. A process as claimed in claim 1, in which the concentration of acrylonitrile in the solvent or solvent mixture is in the range 10 to 50% by volume.

9. A process as claimed in claim 1, in which the ratio of proton-donating solvent to co-solvent is in the range 1:20 to 20:1.